United States Patent [19]

Oohama et al.

[11] 4,143,040
[45] Mar. 6, 1979

[54] PROCESS FOR PRODUCING 17-ACETALS OF 3-ALKOXYESTRA-2,5 (10)-DIEN-17-ONES

[75] Inventors: Tadashi Oohama, Tokyo; Ryozo Yamaguchi, Yokohama; Mamoru Sugano, Kawasaki, all of Japan

[73] Assignee: Mitsubishi Chemical Industries Limited, Tokyo, Japan

[21] Appl. No.: 853,424

[22] Filed: Nov. 21, 1977

[30] Foreign Application Priority Data

Dec. 7, 1976 [JP] Japan .............................. 51/146835

[51] Int. Cl.$^2$ ............................................. C07J 17/00
[52] U.S. Cl. ......................... 260/239.55 C; 260/397.5
[58] Field of Search ..................... 260/239.55 C, 397.5

[56] References Cited

PUBLICATIONS

Organic Reactions in Steroid Chemistry by Fried et al., (1972) Van Nostrand Reinhold Company, New York, N.Y., pp. 51 and 58.

Primary Examiner—Elbert L. Roberts
Assistant Examiner—Robert C. Whittenbaugh
Attorney, Agent, or Firm—Oblon, Fisher, Spivak, McClelland & Maier

[57] ABSTRACT

17-Ketals of 3-alkoxyestra-2,5(10)-dien-17-ones are prepared by reacting 17-ketals of 3-alkoxyestra-1,3,5(10)-trien-17-ones with sodium or potassium, liquid ammonia and a tertiary alcohol in the presence of an alicyclic hydrocarbon and/or an aliphatic hydrocarbon, and a solvent selected from the group consisting of tetrahydrofuran, dioxane and tetrahydropyran.

Yield and selectivity of this reaction are improved by using the 17-ketal of the 3-alkoxyestra-1,3,5(10)-trien-17-one, sodium or potassium, liquid ammonia and the solvent in such proportions that the 17-ketal of the 3-alkoxyestra-1,3,5(10)-trien-17-one is substantially dissolved in the reaction system and that two liquid phases are formed, the lower phase being colored.

22 Claims, 1 Drawing Figure

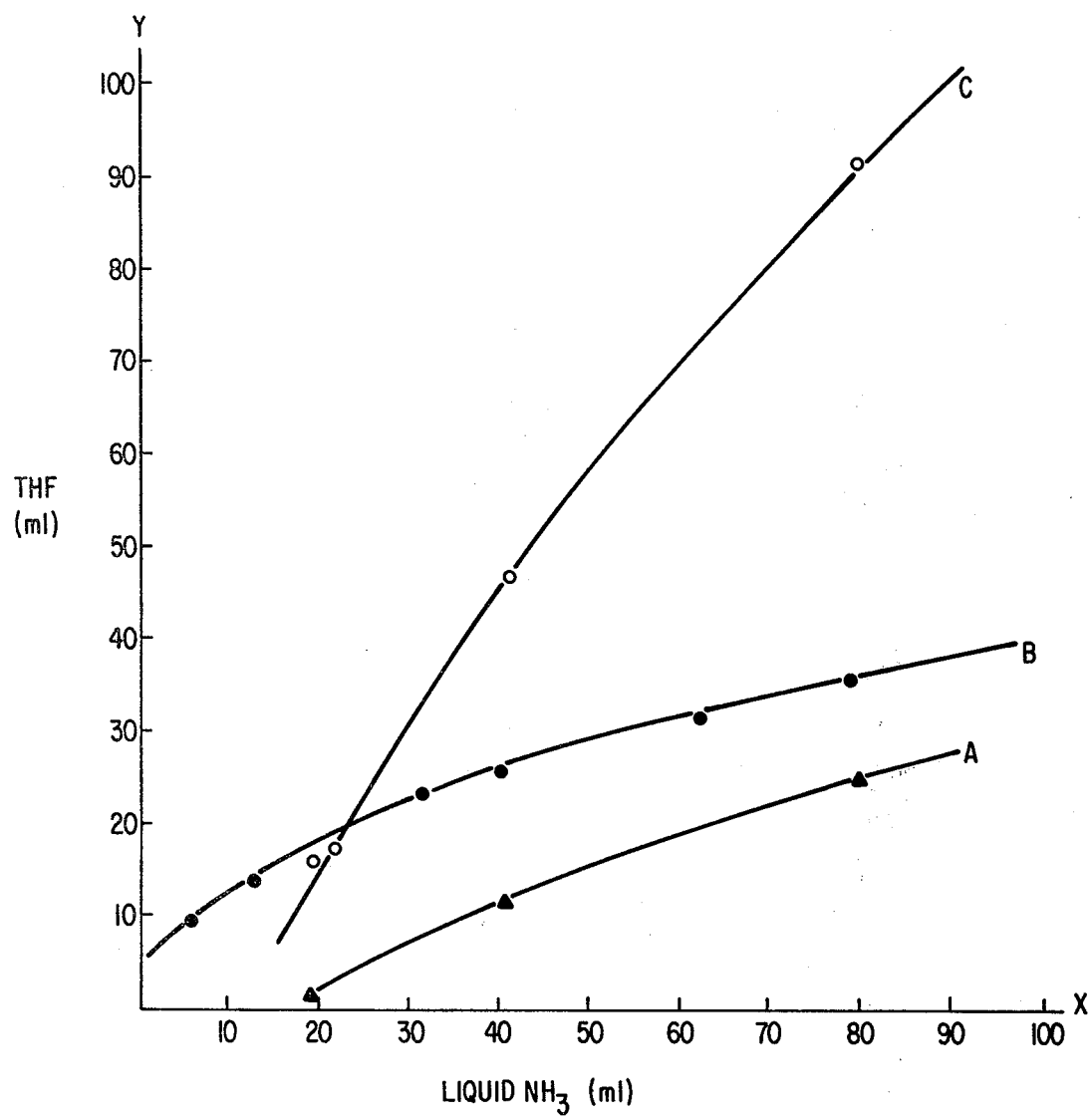

PROCESS FOR PRODUCING 17-ACETALS OF 3-ALKOXYESTRA-2,5 (10)-DIEN-17-ONES

BACKGROUND OF THE INVENTION

1. Field of the Invention

This invention relates to a process for producing 17-acetals of 3-alkoxyestra-2,5(10)-dien-17-ones. (The term acetal as used herein is synonymous with ketal.) More particularly, this invention relates to a commercially practical process for producing 17-acetals of 3-alkoxyestra-2,5(10)-dien-17-ones by Birch reduction of 17-acetals of 3-alkoxyestra-1,3,5(10)-trien-17-ones.

The 17-acetals of the 3-alkoxyestra-2,5-(10)-dien-17-ones are useful as intermediates in the preparation of steroidal hormones such as 19-norethisterone.

2. Description of the Prior Art

Japanese Patent Published 17,030/1960 discloses a process for producing 3-methoxyestra-2,5(10)-dien-17-one ethylene acetal, which comprises reacting 3-methoxyestra-1,3,5(10)-trien-17-one ethylene acetal with lithium or sodium, liquid ammonia and isopropanol in the presence of ethyl ether. This process has the disadvantage of using larger amounts of ethyl ether and liquid ammonia.

It is known that a 1,4-dihydrosteroid e.g., 3-methoxyestra-2,5(10)-dien-17-one diethyl acetal, is produced by reacting an aromatic steroid, e.g., 3-methoxyestra-1,3,5(10)-trien-17-one diethyl acetal with lithium or sodium, liquid ammonia and tert-butanol in the presence of tetrahydrofuran. (See Organic Reactions in Steroid Chemistry edited by John Fried and John A. Edwards, Van Nostrand Reinhold Company, in volume 1 at pages 25–27 and 49–50, and J. Org. Chem., 26 3237–3245 (1961)).

A disadvantage of this purpose is that the use of larger amounts of tert-butanol serving as a proton donor as well as a solvent results in lower reaction rates.

It is believed that impurities present in the starting materials such as 17-acetals of 3-alkoxyestra-1,3,5(10)-trien-17-ones and liquid ammonia, and solvents have a deleterious effect on the conversion of the 17-acetals of the 3-alkoxyestra-1,3,5(10-trien-17-ones to the 17-acetals of the 3-alkoxyestra-2,5(10)-dien-17-ones. This can be avoided by the purification of the starting materials and the solvents, which, however, is not economically attractive because of a decrease in the total yield of the 17-acetals of the 3-alkoxyestra-2,5(10)-dien-17-ones and a loss of the solvents.

It is therefore an object of this invention to provide a process that is capable of producing 17-acetals of 3-alkoxyestra-2,5(10)-dien-17-ones from 17-acetals of 3-alkoxyestra-1,3,5(10)-trien-17-ones in high yields and selectivities. It is another object to produce 17-acetals of 3-alkoxyestra-2,5(10)-dien-17-ones by a process which does not suffer from the disadvantages associated with processes employing larger volumes of a solvent, e.g., ethyl ether, tert-butanol, and liquid ammonia.

Still another object of this invention is to provide a commercially practical process for producing 17-acetals of 3-alkoxyestra-2,5(10-dien-17-ones which permits reliable and reproducible manufacturing operation. These and other objects are accomplished by the invention described herein.

SUMMARY OF THE INVENTION

Briefly stated, that invention is a process for producing 17-acetals of 3-alkoxyestra-2,5(10)-dien-17-ones by the Birch reduction of 17-acetals of 3-alkoxyestra-1,3,5(10)-trien-17-ones which comprises using not more than 90 ml (measured at a boiling point of the reaction system) of liquid ammonia per gram of sodium or potassium, not more than 100 ml (measured at 15° C.) of tetrahydrofuran, dioxane or tetrahydropyran per gram of sodium or potassium, sodium or potassium, and a 17-acetal of a 3-alkoxyestra-1,3,5(10)-trien-17-one in such proportions that the 17-acetal of the 3-alkoxyestra-1,3,5(10)-trien-17-one is substantially dissolved in the reaction system and that two liquid phases are formed in the reaction system, the upper phase consisting mainly of sodium or potassium, and liquid ammonia, and the colored lower phase consisting mainly of tetrahydrofuran, dioxane or tetrahydropyran, liquid ammonia and the 17-acetal of the 3-alkoxyestra-1,3,5(10)-trien-17-one, the Birch reduction being effected in the presence of an alicyclic hydrocarbon and/or an aliphatic hydrocarbon.

DETAILED DESCRIPTION OF THE INVENTION

The reaction embraced by the process of this invention is illustrated by the following reaction scheme:

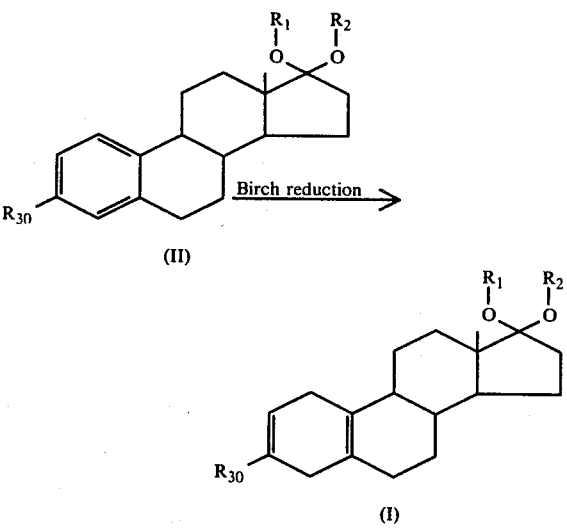

In accordance with the process of this invention, the 17-acetal of the 3-alkoxyestra-2,5(10)-dien-17-one (I) (hereinafter referred to as ESD) is obtained by the Birch reduction of the 17-acetal of the 3-alkoxyestra-1,3,5(10)-trien-17-one (II) (hereinafter referred to as ETA).

In the above-described formulas (I) and (II), $R_1$ and $R_2$ when considered separately are alkyl of 1–10 (preferably 1–5) carbon atoms such as methyl, ethyl, propyl, butyl or the like; $R_1$ and $R_2$ when taken together alkylene of 2–10 (preferably 2–5) carbon atoms such as ethylene, propylene, trimethylene, tetramethylene or the like; and $R_3$ is alkyl of 1–10 (preferably 1–5) carbon atoms such as methyl, ethyl, propyl, butyl or the like.

Representative of ETA which is used in the process of this invention are:

3-methoxyestra-1,3,5(10)-trien-17-one ethylene acetal
3-ethoxyestra-1,3,5(10)-trien-17-one ethylene acetal
3-methoxyestra-1,3,5(10)-trien-17-one dimethyl acetal
3-methoxyestra-1,3,5(10)-trien-17-one diethyl acetal
3-ethoxyestra-1,3,5(10)-trien-17-one diethyl acetal
3-methoxyestra-1,3,5(10)-trien-17-one propylene acetal 3-methoxyestra-1,3,5(10)-trien-17-one tetramethylene acetal Especially preferred is 3-methoxyestra-1,3,5(10-trien-17-one ethylene acetal.

In accordance with the process of this invention, the Birch reduction of ETA is effected using sodium or potassium (preferably sodium) as a reducing agent; a tertiary alcohol e.g., tert-butyl alcohol, tert-amyl alcohol (preferably tert-butyl alcohol) as a proton donor; liquid ammonia; an alicyclic hydrocarbon and/or an aliphatic hydrocarbon; and a solvent which is tetrahydrofuran, dioxane or tetrahydropyran (preferably tetrahydrofuran).

Sodium or potassium is used as a reducing agent. However, the use of potassium on a commercial scale is dangerous because of the vigorous reaction of potassium with water. Therefore, sodium is the preferred reducing agent. It is not preferred to use lithium instead of sodium or potassium because of the low selectivity and the difficulty in controlling the reaction on a commercial scale associated with a higher reaction rate.

The preferred tertiary alcohols are tert-butyl alcohol and tert-amyl alcohol which give the high selectivity. Especially preferred is tert-butyl alcohol.

Slight solubility of ETA in liquid ammonia requires the presence of a solvent which dissolves ETA into the reaction system. Such solvents include tetrahydrofuran, dioxane and tetrahydropyran which readily dissolve ETA. The preferred solvent is tetrahydrofuran because of its low boiling point. In the process of this invention, a combination of sodium, liquid ammonia and tetrahydrofuran will give the best result. Characteristic features of the process of this invention are the amounts of sodium or potassium, liquid ammonia the solvent and ETA to be used, the proportions thereof, and the use of an alicyclic hydrocarbon and/or an aliphatic hydrocarbon.

Criticality of the amounts of the four components to be used and the proportions thereof will be more fully explained in conjunction with the attached drawing which illustrates a change of a phase state with the amounts of liquid ammonia, tetrahydrofuran and 3-methoxyestra-1,3,5(10)-trien-17-one ethylene acetal (hereinafter referred to EMK) or sodium to be used. In the drawing, the X axis represents the amount (ml) of liquid ammonia to be used, which is measured at a boiling point of the system, and the Y axis represents the amount (ml) of tetrahydrofuran to be used, which is measured at 15° C. When the amounts of liquid ammonia and tetrahydrofuran to be used per gram of sodium are in the region above Line A of the drawing, two liquid phases are formed, the upper phase being reddish-copper colored and consisting mainly of sodium and liquid ammonia, and the lower phase consisting mainly of tetrahydrofuran, liquid ammonia and EMK. When they are in the region below Line A of the drawing, a single phase having a reddish-copper to deep blue color is formed.

When they are in the region above Line C of the drawing, the lower phase consisting mainly of tetrahydrofuran, liquid ammonia and EMK is substantially colorless. When they are in the region below Line C of the drawing, the lower phase is deep blue.

When the lower phase consisting mainly of tetrahydrofuran, liquid ammonia and EMK is colorless, sodium is not dissolved in the lower phase. On the other hand, when the lower phase is colored, sodium is dissolved in the lower phase.

When the amounts of liquid ammonia and tetrahydrofuran to be used per gram of EMK are in the region above Line B of the drawing, EMK is completely dissolved in the system. When they are in the region below Line B of the drawing, EMK is not completely dissolved in the system.

In order to increase the rate of reaction, it is essential that EMK be substantially dissolved in the reaction system. When a portion of EMK is present in the form of a solid, the rate of reaction is very low. In order to further increase the rate of reaction, it is essential that sodium be dissolved in the lower phase in which EMK is substantially dissolved.

When sodium is not substantially dissolved in the lower phase in which EMK is substantially dissolved, good contact of the upper and lower phases will be required by means of vigorous stirring which is not economically advantageous. Therefore, it is preferred that the amounts of liquid ammonia and tetrahydrofuran to be used per gram of sodium be in the region below Line C, and that the amounts of liquid ammonia and tetrahydrofuran to be used per gram of EMK be in the region above Line B.

When the amounts of liquid ammonia and tetrahydrofuran to be used per gram of sodium are in the region below Line A, EMK, in many cases, is not completely dissolved in the reaction system. This fact will be explained by slight amounts of liquid ammonia and tetrahydrofuran to be used and by the ratio of sodium to EMK, which will be described below. As apparent from the above, in order to increase the rate of the Birch reduction, it is essential that ETA be substantially dissolved in the reaction system, and that a reducing agent sodium or potassium be dissolved in the lower phase in which ETA is substantially dissolved.

However, in order for the process of this invention to be economically attractive, it is not preferred to use larger amounts of liquid ammonia and the solvent.

The amount of liquid ammonia to be used per gram of sodium or potassium is generally not more than 90 ml, preferably not more than 75 ml and more preferably 60 ml, each being measured at the boiling point of the system.

The amount of the solvent to be used per gram of sodium or potassium is generally not more than 100 ml, preferably not more than 75 ml and more preferably not more than 60 ml, each being measured at 15° C.

In a preferred embodiment of the process of this invention, which is a combination of sodium, EMK, tetrahydrofuran and liquid ammonia, sodium: EMK: tetrahydrofuran: liquid ammonia is 1 g.: 0.5–4.0 g.: 25–100 ml: 25–90 ml and preferably 1 g.: 1.0–2.5 g.: 30–70 ml: 35–70 ml, provided with EMK is substantially dissolved in the reaction system and that two liquid phases are formed, the lower phase being colored. At least 2 gram equivalents of sodium or potassium is used per mole of ETA.

The preferred amount of sodium or potassium to be used is in the range of 3.0 to 30 gram equivalents of sodium or potassium per mole of ETA.

A tertiary alcohol is added in an amount sufficient to give 2 equivalents of proton per mole of ETA. However, it is preferred to add the tertiary alcohol in an amount to give 2 to 15 equivalents of proton per mole of ETA, because an excess of sodium or potassium is generally used.

In the process of this invention, the tertiary alcohol serves substantially as a proton donor.

In general, the tertiary alcohol is added 0.5 to 2 hours after the initiation of the reaction.

In order to avoid a deleterious effect caused by impurities present in the starting materials and the solvent, it is essential the Birch reduction be effected in the presence of an alicyclic hydrocarbon and/or an aliphatic hydrocarbon each optionally having a side chain.

Examples of suitable alicyclic hydrocarbons are those of normally 5-15 (preferably 5-10) carbon atoms, such as cyclopentane, cyclohexane, cycloheptane, cyclooctane, cyclononane, cyclodecane, methylcyclopentane, methylcyclohexane and isopropylcyclohexane.

The preferred alicyclic hydrocarbons are cyclopentane, cyclohexane, cyclooctane and methylcyclohexane.

Examples of suitable aliphatic hydrocarbons are those of normally 5-25 (preferably 5-15) carbon atoms, such as pentane, isopentane, hexane, 2,2-dimethylbutane, heptane, 2-methylhexane, octane, isooctane, nonane and decane. The preferred aliphatic hydrocarbons are hexane, heptane, octane and isooctane.

The amount of the hydrocarbon to be used is in the range of normally 1 to 20 ml, and preferably 2 to 10 ml per gram of ETA.

In contrast to the prior art processes which suffer the drawbacks, such as, low yield and selectivity, and low level of reliability and reproducibility, the process of this invention makes it possible to produce ESD in high yield and selectivity, and with high level of reliability and reproducibility which is essential in a commercial scale operation.

An additional advantage of the process of this invention is efficiency and economy associated with the use of smaller amounts of the solvent and liquid ammonia.

A still another advantage of the process of this invention is ease of purification of the product, which can be achieved by high conversions.

BRIEF DESCRIPTION OF THE DRAWING

The drawing illustrates a change of a phase state with the amounts of liquid ammonia, tetrahydrofuran and EMK or sodium to be used. In the drawing, the X axis represents the amount (ml) of liquid ammonia to be used, which is measured at a boiling point of the system, and the Y axis represents the amount (ml) of tetrahydrofuran to be used, which is measured at 15° C. When the amounts of liquid ammonia and tetrahydrofuran to be used per gram of sodium are in the region above Line A of the drawing, two liquid phases are formed, the upper phase being reddish-copper colored and consisting mainly of sodium and liquid ammonia, and the lower phase consisting mainly of tetrahydrofuran, liquid ammonia and EMK. When they are in the region below Line A of the drawing, a single phase having a reddish-copper to deep blue color is formed.

When they are in the region above Line C of the drawing, the lower phase consisting mainly of tetrahydrofuran, liquid ammonia and EMK is colorless. When they are in the region below Line C of the drawing, the lower phase is deep blue. When the amounts of liquid ammonia and tetrahydrofuran to be used per gram of EMK are in the region above Line B of the drawing, EMK is completely dissolved in the system. When they are in the region below Line B of the drawing, EMK is not completely dissolved in the system.

EXAMPLES

The following examples are presented to further illustrate this invention but are not intended to limit the scope thereof. Unless otherwise stated, all percents are on a molar basis. As used in the description of the examples, the following terms have the following meanings: conversion means a mole of (EMK reacting — EMK remaining) per mole of EMK reacting, generally expressed as a percentage, selectivity means a mole of 3-methoxyestra-2,5(10)-dien-17-one 17-ethylene acetal (hereinafter referred to as MEE) which is formed per mole of EMK reacting, generally expressed as a percentage.

EXAMPLE 1

A 500 ml., three-necked round bottom glass flask, fitted with an ammonia gas inlet tube, an agitator and a 200 ml dropping funnel having a scale is charged with 150 ml of liquid ammonia through the dropping funnel into which liquid ammonia, after being vaporized, is introduced. Thereafter, the three-necked flask is charged with 5.0 g. of crude EMK containing impurities which have a deleterious effect on the conversion of EMK to MEE, 2.5 g. of sodium, 125 ml of tetrahydrofuran and 30 ml of n-octane.

The reaction mixture is stirred at about 200 rpm for one hour. At the end of this period, a mixture of 5 ml of tetrahydrofuran and 10 ml of tert-butanol is added over a period of 5 minutes and then stirring is continued for 2 hours. At the end of this period, liquid ammonia is distilled off in a water bath and then tetrahydrofuran is distilled off in vacuo at a temperature below 30° C. to yield a crystalline solid which is extracted with 100 ml of benzene. The benzene layer is washed with water, dried, distilled in vacuo at a temperature below 40° C. to remove benzene and then dried to give 5.0 g. of crude MEE. Gas chromatographic analysis indicated a 99.6% conversion and a 92.3% selectivity.

EXAMPLE 2

Using 5.0 g. of crude EMK as used in Example 1, 2.5 g. of sodium, 125 ml of tetrahydrofuran, 150 ml of liquid ammonia and 15 ml of n-decane, Example 1 is repeated. Gas chromatographic analysis indicated a 99.4% conversion and a 91.6% selectivity.

EXAMPLE 3

Using 5.0 g. of crude EMK as used in Example 1, 2.5 g. of sodium, 125 ml of tetrahydrofuran, 150 ml of liquid ammonia and 10 ml of cyclohexane, Example 1 is repeated. Yield of crude MEE is 5.0 g. Gas chromatographic analysis indicated a 98.8% conversion and a 92.3% selectivity.

REFERENCE EXAMPLE

This reference example illustrates that when the Birch reduction is effected in the absence of a hydrocarbon using crude EMK a sufficient conversion is not obtained. Using 5.0 g. of crude EMK as used in Example 1, 2.5 g. of sodium, 125 ml of tetrahydrofuran and 150 ml of liquid ammonia, Example 1 is repeated.

Yield of crude MEE is 5.0 g.

Gas chromatographic analysis indicated a 95.3% conversion and a 92.5% selectivity.

What is claimed as new and intended to be covered by letters patent is:

1. In a process for producing a 17-ketal of 3-alkoxy estra-2,5(10)-dien-17-one having the formula (I):

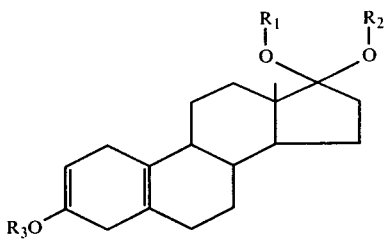

wherein $R_1$ and $R_2$ when considered separately are $C_1$-$C_{10}$ alkyl; $R_1$ and $R_2$ when taken together are $C_2$-$C_{10}$ alkylene; and $R_3$ is $C_1$-$C_{10}$ alkyl,
which comprises reacting a 17-ketal of 3-alkoxyestra-1,3,5(10-trien-17-one having the formula (II):

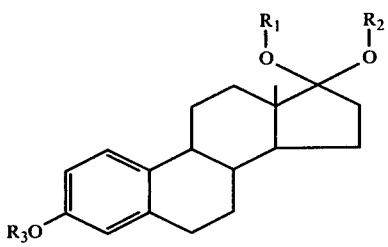

wherein $R_1$, $R_2$ and $R_3$ are as defined above, with sodium or potassium, liquid ammonia and a tertiary alcohol in the presence of a solvent selected from the group consisting of tetrahydrofuran, dioxane and tetrahydropyran, the improvement which comprises using not more than 90 ml (measured at the boiling point of the system) of liquid ammonia per gram of sodium or potassium, not more than 100 ml (measured at 15° C.) of said solvent per gram of sodium or potassium, sodium or potassium, and said 17-ketal of 3-alkoxyestra-1,3,5(10)-trien-17-one in such proportions that said 17-ketal of 3-alkoxyestra-1,3,5(10)-trien-17-one is substantially dissolved in the reaction system and that two liquid phases are formed in the reaction system, the upper phase consisting mainly of sodium or potassium, and liquid ammonia, the colored lower phase consisting mainly of said solvent, liquid ammonia and said 17-ketal of 3-alkoxyestra-1,3,5(10)-trien-17-one, and effecting said reaction in the presence of at least one of an alicyclic hydrocarbon and an aliphatic hydrocarbon.

2. The process of claim 1, wherein said 17-ketal of 3-alkoxyestra-1,3,5(10)-trien-17-one is 3-methoxyestra-1,3,5(10)-trien-17-one ethylene ketal.

3. The process of claim 1, wherein said solvent is tetrahydrofuran.

4. The process of claim 1, wherein said tertiary alcohol is tert-butyl alcohol or tert-amyl alcohol.

5. The process of claim 4, wherein said tertiary alcohol is tert-butyl alcohol.

6. The process of claim 1, wherein sodium is used.

7. The process of claim 1, wherein 3-methoxyestra-1,3,5(10)-trien-17-one ethylene ketal, liquid ammonia, tetrahydrofuran and sodium are used.

8. The process of claim 1, wherein not more than 75 ml of liquid ammonia per gram of sodium or potassium, and not more than 75 ml of said solvent per gram of sodium or potassium are used.

9. The process of claim 8, wherein not more than 60 ml of liquid ammonia per gram of sodium or potassium, and not more than 60 ml of said solvent per gram of sodium or potassium are used.

10. The process of claim 1, wherein at least 2 gram equivalents of sodium or potassium per mole of said 17-ketal of 3-alkoxyestra-1,3,5(10)-trien-17-one are used.

11. The process of claim 10, wherein 3.0 to 10 gram equivalents of sodium or potassium per mole of said 17-ketal of 3-alkoxyestra-1,3,5(10)-trien-17-one are used.

12. The process of claim 1, wherein said tertiary alcohol is used in an amount sufficient to give at least 2 equivalents of protons per mole of said 17-ketal of 3-alkoxyestra-1,3,5(10)-trien-17-one.

13. The process of claim 12, wherein said tertiary alcohol is used in an amount sufficient to give 2 to 15 equivalents of protons per mole of said 17-ketal of 3-alkoxyestra-1,3,5(10)-trien-17-one.

14. The process of claim 1, wherein the tertiary alcohol is added 0.5 to 2 hours after the initiation of the reaction.

15. The process of claim 1, wherein the alicyclic hydrocarbon contains 5 to 15 carbon atoms and said aliphatic hydrocarbon contains 5 to 25 carbon atoms.

16. The process of claim 1, wherein the amount of said hydrocarbon is in the range of 1 to 20 ml per gram of said 17-ketal of 3-alkoxyestra-1,3,5(10)-trien-17-one.

17. The process of claim 16, wherein said amount is 2 to 10 ml per gram of said 17-ketal of 3-alkoxyestra-1,3,5(10)-trien-17-one.

18. The process of claim 1, wherein said 17-ketal of 3-alkoxyestra-1,3,5(10)-trien-17-one is selected from the group consisting of
3-methoxyestra-1,3,5(10)-trien-17-one ethylene ketal,
3-ethoxyestra-1,3,5(10)-trien-17-one ethylene ketal,
3-methoxyestra-1,3,5(10)-trien-17-one dimethyl ketal,
3-methoxyestra-1,3,5(10)-trien-17-diethyl ketal,
3-ethoxyestra-1,3,5(10)-trien-17-one diethyl ketal,
3-methoxyestra-1,3,5(10-trien-17-one propylene ketal and
3-methoxyestra-1,3,5(10)-trien-17-one tetramethylene ketal.

19. The process of claim 1, wherein said alicyclic hydrocarbon is selected from the group consisting of cyclopentane, cyclohexane, cycloheptane, cyclooctane, cyclononane, cyclodecane, methylcyclopentane, methylcyclohexane and isopropylcyclohexane.

20. The process of claim 1, wherein said alicyclic hydrocarbon is selected from the group consisting of cyclopentane, cyclohexane, cyclooctane and methylcyclohexane.

21. The process of claim 1, wherein said aliphatic hydrocarbon is selected from the group consisting of pentane, isopentane, hexane, 2,3-dimethylbutane, heptane, 2-methylhexane, oxtane, isooctane, nonane and decane.

22. The process of claim 1, wherein said aliphatic hydrocarbon is selected from the group consisting of hexane, heptane, octane and isooctane.

* * * * *